(12) United States Patent
Tsinberg

(10) Patent No.: US 7,595,157 B2
(45) Date of Patent: Sep. 29, 2009

(54) MICROARRAYS UTILIZING HYDROGELS

(75) Inventor: Pavel Tsinberg, Carlsbad, CA (US)

(73) Assignee: Biocept, Inc., San Diego, CA (US)

( * ) Notice: Subject to any disclaimer, the term of this patent is extended or adjusted under 35 U.S.C. 154(b) by 467 days.

(21) Appl. No.: 10/922,391

(22) Filed: Aug. 19, 2004

(65) Prior Publication Data

US 2006/0040274 A1 Feb. 23, 2006

(51) Int. Cl.
*C12Q 1/68* (2006.01)

(52) U.S. Cl. .................. 435/6; 506/23; 506/7; 524/916

(58) Field of Classification Search ........................ None
See application file for complete search history.

(56) References Cited

U.S. PATENT DOCUMENTS

| | | | |
|---|---|---|---|
| 4,794,090 A | 12/1988 | Parham et al. | |
| 5,169,720 A | 12/1992 | Braatz et al. | |
| 5,175,229 A | 12/1992 | Braatz et al. | |
| 5,403,750 A | 4/1995 | Braatz et al. | |
| 5,624,711 A | 4/1997 | Sundberg et al. | |
| 5,981,734 A | 11/1999 | Mirzabekov et al. | 536/25.3 |
| 6,083,393 A * | 7/2000 | Wu et al. | 210/500.35 |
| 6,174,683 B1 * | 1/2001 | Hahn et al. | 435/6 |
| 6,372,813 B1 * | 4/2002 | Johnson et al. | 522/114 |
| 6,569,674 B1 * | 5/2003 | McGarry et al. | 435/287.2 |
| 6,797,393 B2 * | 9/2004 | Qiao et al. | 428/478.2 |
| 2003/0096257 A1 | 5/2003 | Shinoki et al. | 435/6 |
| 2003/0108917 A1 | 6/2003 | Huh et al. | 435/6 |
| 2003/0124371 A1 | 7/2003 | Um et al. | 428/522 |
| 2003/0138649 A1 | 7/2003 | Qiao et al. | 428/478.3 |
| 2003/0170474 A1 | 9/2003 | Qiao et al. | 428/478.2 |

FOREIGN PATENT DOCUMENTS

| | | |
|---|---|---|
| EP | 0420053 A1 | 4/1991 |
| WO | WO 02/059372 A2 | 10/2000 |

* cited by examiner

*Primary Examiner*—Jeffrey S. Lundgren
(74) *Attorney, Agent, or Firm*—Fitch, Even, Tabin & Flannery

(57) ABSTRACT

A method of making a microarray by coating a flat substrate with a polymerizable hydrogel layer which contains anchoring moieties dispersed uniformly therethroughout. Following curing, a continuous layer of uniform thickness is securely attached to the upper surface of the substrate through an array region thereof. A plurality of different probes are then attached to create microspots at distinct spatial locations on the surface of this slab layer by linking the probes to the anchoring moieties in the cured hydrogel. Such anchoring moieties may employ linking systems such as organic chelators, that are activated by copper or some other metal, and complementary pairs such as avidin-biotin.

1 Claim, No Drawings

MICROARRAYS UTILIZING HYDROGELS

FIELD OF THE INVENTION

The present invention relates generally to methods for fabricating microarrays and the resulting products, and more particularly to methods for fabricating microarrays upon a suitable substrate or chip by substantially uniformly coating a region of such substrate with a polymerizable hydrogel layer.

BACKGROUND OF THE INVENTION

Microarrays are used in bioassaying for the presence and/or quantitative amount of a target material in a biological sample; they constitute a growing field that is sometimes referred as surface-based assays wherein the target material, or a molecule representative of such, is captured on a solid support and then detected. Such DNA microarrays have now become widely accepted for the study of gene expression and other genotyping functions as a result of their capacity to simultaneously monitor a large number of genes. For example, a large number of different probe sequences can be bound at distinct spatial locations or microspots across a microarray surface, and each such microspot may contain a different probe. When such a microarray is hybridized with a solution containing labeled sample material, hybridization occurs between complimentary DNA strands at the various different microspots of the array whenever the target is present. After washing to remove unbound material, the character of the labels, e.g., fluorescent, is then used to determine the intensity of labeled material at each microspot; this imaging can provide a measure of the quantitative amount of the particular target that was present in the sample.

Such arrays have also been fabricated to present other moieties, such as proteins including antibodies, and haptens or aptamers, for binding to target materials. These surface-based assays can also be used for ELISAs. Overall, the use of such microassay chips has been replacing gel electrophoresis as the method of choice for bioassaying, and this trend is believed very likely to continue as the field of proteomics becomes more advanced.

For a microassay chip to be effective for such bioassay applications, it should have the ability to immobilize a satisfactory amount of analyte or target material to be sequestered from a relevant sample; it is in this manner that a signal of satisfactory magnitude is provided when the chip is subjected to subsequent reading. The chip, of course, should also be capable of being fabricated so as to be highly uniform, in order to produce reproducible results from assay to assay.

Many microarray chips have been developed in the past decade where probes have been immobilized on a modified glass substrate, a silicon substrate, or the like, at distinct spatial locations, to create an array which presents a large number of different probes. Initially microarrays were developed as a two-dimensional form wherein probes were directly bound on the surface on the substrate. More recently three-dimensional microarrays have been developed using hydrogel materials wherein the microspots may resemble minute hemispheres, the porous structures of which present a three-dimensional framework or matrix. Microarrays of this type are described in U.S. Pat. No. 6,174,683 and in published International Application WO 02/059372.

U.S. published application 2003/0124371 discloses the use of water-swellable hydrophilic hydrogels which are considered to be particularly useful for immobilizing polypeptide analytes onto an absorbent layer, which layer is engineered by varying the ratio of hydrophilic moieties and hydrophobic moieties in the hydrogel. The hydrophilic and hydrophobic monomers which make up the hydrogel are cross-linked to create a desired polymer. As an example, an aluminum substrate is coated with silicon dioxide and then treated with an alkylsilane before the monomers are applied to a plurality of addressable locations (microspots) and then cross-linked by radiation. Probes are added to each microspot on the chip, using a binding buffer, and the loaded chip is incubated for thirty minutes. Washing then readies the chip for use in an assay.

U.S. published application 2003/0138649 teaches the fabrication of microarrays particularly suited for attaching proteins which will serve as probes or capture agents using a gelatin-based substrate. A suitable substrate such as glass or silicon or photographic paper is coated with a solution of type IV gelatin; for example, gelatins were coated onto reflective photographic paper and then chill-set and dried. The plates having the overall gelatin coating are then microspotted to attach bi-functional compounds, e.g. goat anti-mouse antibody IgG, which has a group that will link to the gelatin and a second functional group that is capable of interacting with high specificity with a protein. In a related U.S. published application, No. 2003/0170474, a silicon wafer or glass plate is treated first with an alkylsilane and then dipped in a solution of gelatin. The gelatin-coated substrate is then dipped in a solution of polyethyleneimine (PEI). The surface was reported to have a relatively low nonspecific binding capacity for proteins and that it could be used as a microarray substrate by affixing protein capture agents at microspots spaced across the surface.

U.S. published application 2003/0096257 teaches the making of DNA chips by coating a glass slide with an aminoalkylsilane and then attaching vinylsulfonyl groups across the entire surface by bonding to the amino groups. Oligonucleotides with linkers were then spotted onto the reactive plate and suitably incubated to secure the linkage to produce a DNA chip useful for a hybridization analysis.

Although there may be various advantages to these methods of making of biochips or the like, each of them is not without its disadvantages. Accordingly, the search has continued for still better methods for the fabrication of such microarrays with emphasis often being concentrated on the employment of hydrogels in such microarrays.

SUMMARY OF THE INVENTION

It has now been found that microarrays can be fabricated by providing a substrate, the upper surface of which is functionalized with organic molecules, and coating that surface with a polymerizable hydrogel layer which contains anchoring moieties disbursed uniformly throughout so as to cover a continuous region of the surface that will serve as a microarray. After curing the coated substrate so as to polymerize the coated hydrogel layer, a variety of different probes are attached at distinct spatial locations on the surface to form microspots, by linking the probes to the anchoring moieties that are present in the cured hydrogel layer. If desired, the areas surrounding the microspots can be passivated. However, when the hydrogel is based upon PEG or PPG (or a copolymer thereof) and a polyisocyanate cross linker, and when the anchoring moieties being used are organic chelators, nonspecific binding should not be high so passivation may not be felt to be needed.

In one particular aspect, the invention provides a method of making a microarray, which method comprises the steps of: providing a substrate having an upper surface that is functionalized with organic molecules, coating said surface with a polymerizable hydrogel layer so as to completely cover an array region of the surface, said layer including anchoring moieties dispersed uniformly therethroughout, curing said coated substrate to polymerize said hydrogel layer, and subsequently attaching a plurality of different probes to said coated surface at distinct spatial locations thereon by linking said probes to said anchoring moieties which are present within said cured hydrogel layer.

In another particular aspect, the invention provides a microarray which comprises: a substrate having an upper surface that is functionalized with organic molecules, a polymerized hydrogel layer completely covering an array region of said surface, said layer including anchoring moieties dispersed uniformly therethroughout, and a plurality of different probes attached to said hydrogel coating layer on said surface at distinct spatial locations thereon, said probes being linked to said anchoring moieties in said polymerized hydrogel layer and regions of said coating layer surrounding said locations being essentially free from probes.

DETAILED DESCRIPTION OF THE PREFERRED EMBODIMENTS

A substrate is used in the form of a flat plate or the like which can be made of any suitable material commonly used in a chemical laboratory; examples include, glass, quartz, silicon, silica, stainless steel and inert polymers, such as polyethylenes, polypropylenes, polyacrylics, polycarbonates and the like, as well known in the art. The plate may be optionally coated with a reflective layer, as also well known in this art. The reflective layer should preferably cover substantially all of the surface region of the substrate where the probes will be attached, i.e. the array region; however, often a reflective coating that covers the entire upper surface of the substrate is used for manufacturing convenience. The reflective layer may be a reflective metal, e.g., aluminum, silver, gold, rhodium etc., which provides a mirrored layer. By reflective metal is meant a metal that reflects at least 90% of incident light in the wavelength region of interest, generally visible (400-800 nm), and possibly including longer wavelengths in the near infrared, such as 800-1100 nm, with very little (at or near 0%) light being refracted into the medium. Such a thin metal layer may be provided using any of the conventional vapor coating or other coating methods well known in the art for providing such mirror coatings. The thickness of the layer is not of particular consequence so long as there is continuity, but a layer about 0.01 micron to about 15 microns thick is generally used when such a layer is included.

One embodiment of the invention includes a microarray which comprises: a solid, flat substrate having an upper surface that is functionalized with organic molecules, a polymerized hydrogel layer completely covering an array region of said surface, said layer including anchoring moieties dispersed uniformly therethroughout, said hydrogel comprising (a) PEG or PPG or a copolymer thereof of a molecular weight between about 500 and about 30,000 daltons and (b) difunctional and/or polyfunctional isocyates, and a plurality of different probes attached to said coated surface at distinct spatial locations thereon to create a plurality of microspots, said probes being linked to said anchoring moieties in said polymerized hydrogel layer and regions surrounding said microspots being essentially free from probes.

When the substrate is used to create microarrays to be employed in microassays that employ labels or tags which emit light either spontaneously or in response to excitation, for example, fluorescent, luminescent or phosphorescent labels, light emitted from these various labels will have a known wavelength. Pending U.S. application Ser. No. 10/664,248, filed Sep. 16, 2003, now U.S. Pat. No. 7,198,901, issued on Apr. 3, 2007, the disclosure of which is incorporated herein by reference, teaches that background artifact emissions at the location of a microspot or other such probe location can be very substantially reduced by employing a dielectric layer atop the reflective metal layer which yields substantial cancellation of certain wavelengths. Transparent dielectric layers made of materials, such as silicon monoxide and/or silicon dioxide, may be employed which will normally range in thickness between about 0.1 and about 5 microns. If the upper surface of the substrate is uniformly coated with such a thin, metallic, mirrored layer, then the entire upper surface is preferably coated with this uniform dielectric layer. The deposition of such very thin dielectric films of silica, alumina, magnesium fluoride or the like from a vapor atmosphere is well known in the art.

Once such a thin dielectric layer is in place, the upper surface of the dielectric layer is preferably treated chemically to promote strong attachment of the hydrogel that will be used to provide the array of probes or capture agents. The dielectric surface is preferably derivatized with a suitable reagent, such as PEI, polylysine or an aminoalkylsilane, that will cover the entire surface with pendent amino groups that then can be used for strong attachment of reactive molecules, as is also well known in this art. Examples of such silane coupling agents include aminopropyltriethoxysilane, N-β-(aminoethyl)-α-aminopropyltrimethoxysilane, and N-β-(aminoethyl)-α-aminopropylmethyldimethoxysilane.

Microarrays where three-dimensional microspots of hydrogels are employed to serve as holders for the probes or capture agents are described in U.S. Pat. No. 6,174,683 and in published international applications WO 09/059,372, entitled "Three Dimensional Format Biochips", and WO 02/081662, entitled "Methods and Gel Compositions For Encapsulating Living Cells and Organic Molecules".

A polymerizable hydrogel coating of choice is preferably one made using isocyanate-functional prepolymers that are prepared from relatively high molecular weight polyoxyalkylene diols or polyols by reacting them with difunctional and/or polyfunctional isocyanate compounds. Preferred prepolymers are ones made from polyoxyalkylene diols or polyols that comprise homopolymers of ethylene oxide units or block or random copolymers containing mixtures of ethylene oxide units and propylene oxide or butylene oxide units. In the case of such block or random copolymers, at least 75% of the units are preferably ethylene oxide units. Such polyoxyalkylene diol or polyol molecular weight is preferably from 500 to 30,000 daltons, and in some instances, a molecular weight of at least about 5,000 daltons is more prefered. Suitable prepolymers may be prepared by reacting selected polyoxyalkylene diols or polyols with a polyisocyanate so that essentially all of the hydroxyl groups are capped with polyisocyanate, as described in more detail hereinafter. Generally, polyethylene glycol (PEG), polypropylene glycol (PPG) or copolymers thereof are preferred. The isocyanate-functional prepolymers preferably contain active isocyanates in an amount of about 0.1 meq/g to about 1 meq/g, and more preferably about 0.2 meq/g to about 0.8 meq/g. If relatively low molecular weight prepolymers, e.g. less than 2,000 daltons, are used, they preferably contain a relatively high isocyanate content (about 1 meq/g or even higher). However, the polymerization rate of such smaller prepolymers may require more precise control to avoid too rapid polymerization. Moreover, prepolymers with a fairly high isocyanate content may have a relatively high content of free amines after polymerization, and the positive charges on such amine functionalities, at neutral pH, may increase non-specific binding of negatively charged biomolecules with the potential of resulting in higher levels of undesirable background signals. Thus, higher molecular weight prepolymers which contain a relatively low isocyanate content may generally be preferred.

Such high molecular weight prepolymers are often prepared by either of two general methods, but others as known in the art can also be used: (1) a polyol (triol or higher) having a molecular weight of at least 2000 daltons, is reacted with a polyisocyanate such as isophorone diisocyanate, or (2) a diol having a molecular weight of at least 2000 daltons is reacted with a polyisocyanate and a cross-linking agent, such as glycerol, trimethylolpropane, trimethylolethane, triethanolamine or an organic triamine.

Aromatic, aliphatic or cycloaliphatic polyisocyanates may be used. High molecular weight aliphatic isocyanate-capped prepolymers typically gel to a hydrated polymer state in about 20 to 90 minutes, whereas prepolymers capped with aromatic polyisocyanates gel much more rapidly. Examples of suitable bi- and multi-functional isocyanates are as follows: 4,4'-methylenebis-(phyenyl isocyanate) (MDI), toluene-2,4-diisocyanate, toluene-2,6-diisocyanate (a mixture of which isomers is commercially sold as TDI), isophorone diisocyanate, ethylene diisocyanate, ethylidene diisocyanate, propylene-1,2-diisocyanate, cyclohexylene-1,2-diisocyanate, cyclohexylene-1,4-diisocyanate,-phenylene diisocyanate, 3,3"-diphenyl-4,4"-biphenylene diisocyanate, 1,6-hexamethylene diisocyanate, 1,4-tetramethylene diisocyanate, 1,10-decamethylene diisocyanate, cumene-2,4-diisocyanate, 1,5-naphthalene diisocyanate, methylene dicyclohexyl diisocyanate, 1,4-cyclohexylene diisocyanate, p-tetramethyl xylylene diisocyanate, p-phenylene diisocyanate, 4-methoxy-1,3-phenylene diisocyanate, 4-chloro-1,3-phenylene diisocyanate, 4-bromo-1,3-phenylene diisocyanate, 4-ethoxyl-1,3-phenylene diisocyanate, 2,4-dimethyl-1,3-phenylene diisocyanate, 2,4-dimethyl-1,3-phenylene diisocyanate, 5,6-dimethyl-1,3-phenylene diisocyanate, 1,4-diisocyanatodiphenylether, 4,4'-diisocyanatodi-phenylether, benzidine diisocyanate, 4,6-dimethyl-1,3-phenylene diisocyanate, 9,10-anthracene diisocyanate, 4,4'-diisocyanatodi-benzyl, 3,3'-dimethyl-4,4'-diisocyanatodiphenylmethane, 1,6-dimethyl-4,4'-diisocyanatodiphenyl, 2,4-diisocyanatostibene, 3,3'-dimethoxy-4,4'-diisocyanatodiphenyl, 1,4-antracenediisocyanate, 2,5-fluoronediisocyanate, 1,8-naphthalene diisocyanate, 2,6-diisocyanatobenzluran, 2,4,6-toluene triisocyanate, p,p',p"-triphenylmethane triisocyanate, trifunctional trimer (isocyanurate) of isophorone diisocyanate, trifunctional biuret of hexamethylene diisocyanate, trifunctional trimer (isocyanurate) of hexamethylene diisocyanate, polymeric 4,4'-diphenylmethane diisocyanate, xylylene diisocyanate and m-tetramethyl xylylene diisocyanate.

Capping of the selected diols or polyols with polyisocyanates to form prepolymers may be effected using stoichiometric amounts of reactants. The isocyanate-to-hydroxyl group ratio may vary as known in this art but should preferably be about 1 to about 3, and more preferably about 1.2 to about 2.2. The capping reaction may be carried out using any suitable conditions, such as at about 20° C. to about 150° C., under dry nitrogen, for about 2 hours to about 14 days, and preferably in the absence of a catalyst. The preferred temperature is about 60° C. to 100° C., and the reaction terminates when the isocyanate concentration approximates theoretical values.

Preferred prepolymers include polyethylene glycol that is end-capped with toluene diisocyanate; a copolymer of ethylene oxide and propylene oxide (optionally with trimethylolpropane) and toluene diisocyanate; toluene diisocyanate-polyethylene glycol-trimethylopropane, methylene diisocyanate-methylene homopolymer; polymeric methylene diisocyanate-polyethylene glycol; polymer of ethylene oxide-propylene oxide-trimethylolpropane and isophorone diisocyanate, and polyethylene glycol trilactate and toluene diisocyanate. Suitable prepolymers of the above types are available from Dow Chemical Company as HYPOL PreMA® G-50, HYPOL® 2000, HYPOL® 3000, HYPOL® 4000 and HYPOL® 5000, which formulations generally include copolymers of polyethylene oxide and a minor amount of polypropylene oxide. Others are available under the trademark Urepol from EnviroChem Technologies, and comparable prepolymers can be prepared from commercially available feedstocks.

All things considered, the main chain of the hydrogel polymer is preferably comprised of polyethylene glycol, polypropylene glycol, or a copolymer of polyethylene glycol and polypropylene glycol. Non-ionic, hydrophilic properties of polyethylene glycol and polypropylene glycol hydrogels provide for low levels of non-specific binding of analyte to the hydrogel and also provide good compatibility with biomolecules that may be immobilized therewith so as to maintain native conformation and bioreactivity thereof. Polyurethane-based isocyanate-functional hydrogels of this general type are described in U.S. Pat. No. 3,939,123 (Mathews, et al.), U.S. Pat. No. 4,110,286 (Vandegaer, et al.) and U.S. Pat. No. 4,098,645 (Hartdegan, et al.).

In a preferred embodiment, substrates for microarrays are made using an isocyanate-functional hydrogel that is based on a diol or triol of a high molecular weight polyethylene oxide, polypropylene oxide, or a copolymer of polyethylene oxide and polypropylene oxide, capped with water-active diisocyanates, and which may be optionally lightly crosslinked with a suitable crosslinker. As earlier indicated, it is preferred that the quantity of active isocyanates present in the prepolymer is preferably between about 0.1 and about 1 meq/g. Generally preferred diisocyanates include the aromatic-based diisocyanates, toluene diisocyanate (TDI) and methylene diphenyl-isocyanate (MDI) and the aliphatic diisocyanate, isophorone diisocyanate. About 0.01% to about 15% of the reactive isocyanates in the prepolymer are generally employed to bind the coating to the substrate, which leaves ample sites for immobilizing anchoring entities. The prepolymer may be preformulated in a water-miscible organic solvent, and polymerization generally takes place by the formation of urea linkages which occur upon the simple addition of water.

The hydrogel coating that is applied contains anchoring moieties dispersed uniformly throughout, which moieties are used to either directly or indirectly anchor the probes as part of a microarray. They may be dissolved in aqueous solution and mixed with a prepolymer to begin the polymerization reaction. Examples of suitable anchoring moieties include organic chelators and organic linkers, which may be one-half of a pair of complementary linkers, such as streptavidin and biotin, the other member of which pair is then attached to the probe of interest. When organic chelators are mixed as one component of the polymerizable layer (thus becoming dispersed uniformly throughout the cured layer), following its curing, the coating is treated with water-soluble metal ions in aqueous solution so that metal cations become bound to the organic chelators, usually at 3 or 4 points. When this system is used, the probes are likewise attached to organic molecules that will complex with these metal ions which have now activated the chelators in the cured coating layer.

The thickness of the cured hydrogel layer or slab may vary from about 1 micron to about 1000 microns; it is preferably at least about 5 microns thick. For example, when tridentate or tetradentate organic chelators, such as iminodiacetic acid (IDA) or nitrilotriacetic acid (NTA), are employed, they may be included in the coating composition at a concentration of between about 50 mM and about 1 mM so that will be an adequate amount of these anchoring moieties distributed uniformly throughout the entire coating layer that will cover the region of the array.

Once the hydrogel layer or slab has been applied, it is allowed to cure until the formulation is essentially fully crosslinked. Because application and curing can be carried out under closed conditions, problems with solvent evaporation may be essentially eliminated (as opposed to a situation wherein one would deposit microspots in a regular pattern on a flat plate); thus, a broader range of solvents and hydrogel formulations are available without encountering environmental or other fabrication difficulties. Likewise, there should be very little variability between coated plates, because the casting/molding/coating step can be made extremely uniform, and because a large number of plates can be coated at once, many limitations inherent in mechanical spotting are likewise obviated.

Once the slide has been fully cured, i.e., the crosslinking having been essentially completed, it is washed to remove any organic chelators or other organic linkers that have not been bound to the hydrogel and also to remove the solvents used in formulating and/or applying the coating composition. When the anchoring moieties are organic chelators, the coated substrates may be incubated with solutions of, for example, copper nitrate or nickel nitrate. As a result, copper or nickel ions from such a solution become bound to the chelators, which is referred to in the art as activating the chelators. The coated substrates can then be optionally dried and stored for an indefinite period of time. If such drying is effected, rehydration of all of the coating or at least those regions where microspots will be located is preferably carried out before or as the microarray is being created.

Biological materials that are employed as capture agents or probes can be any of a wide variety well known in this art. They may run the gamut from DNA sequences and peptides through much larger molecules, such as antibodies; even living cells may be attached at distinct spatial locations to the porous hydrogel using appropriate complementary linkers. May other such binding pairs are disclosed in the aforementioned patents and published international applications in addition to the chelators and biotin-avidin mentioned herein.

In an usual assay, the microarray is exposed to a solution, usually aqueous, containing a sample of biological material under hybridization/binding conditions; the solution contains potential targets which have been tagged or labeled, either with a reporter or signal material or with a linker that will subsequently sequester a reporter material, and incubated. Label or tag is used to refer to a substituent that can be attached to a target, e.g., a nucleic acid sequence, which enables its detection and/or quantitation. Examples include radiolabels such as $^{32}$p, $^{33}$p, and $^{35}$S; colorimetric indicators, such as fluorescent, chemiluminescent or colored compounds; ligands such as biotin; and chemical groups that are distinguishable by mass or other spectroscopic properties. More specific examples of suitable labels include xanthine dyes, rhodamine dyes, naphtylamines, benzoxadiazoles, stilbenes, pyrenes, acridines, Cyanine 3 (Cy-3) and Cyanine 5 (Cy-5). When the target is nucleic acid, a label is preferably introduced into analyte nucleic acid by incorporation directly as a part of a primer; however, indirect addition by chemical reaction or, enzymatic reaction, or by hybridization or annealing of a label with an intermediate ligand may also be used. For simplicity and efficiency, it may be preferred to simply employ light-emitting labels of the fluorescent, luminescent or phosphorescent variety in the analyte sample to be used in the hybridization step. Although binding pairs, such as avidin-biotin, may be used to subsequently add labels, these substrates may provide particular advantages to create microarrays for use in assays where labels are already covalently bonded to the target biological material in the sample solution being used in the incubation step. Fluorescent labels such as Cy-3 and Cy-5 are examples of such labels commonly employed.

Following the incubation of the microarray with a sample solution over a suitable period, washing is carried out, usually repeatedly, as is well known and common in this art; then the microarray is usually dried before being subjected to imaging. When labels are used that emit light, either spontaneously or when stimulated, there are numerous commercially available photometers that may be employed for imaging. For example, U.S. Pat. No. 5,672,880 discloses a fluorescence imaging system which collects the emitted fluorescent light and directs the collected light onto a photodetector to produce a signal, using a laser beam to stimulate the fluorescence. Published U.S. Application 2002/0109841 discloses a scanning spectrophotometer for high throughput fluorescence detection, wherein the light is collected and transmitted to a photomultiplier tube (PMT) that feeds signals to a processing unit.

The following Examples are presented to provide the best mode presently known for carrying out the invention; however, it should be understood that these Examples are presented for purposes of illustration only and should not considered to be in any way limiting upon the scope of the invention which is defined by the claims that appear at the end hereof.

EXAMPLE 1

A standard laboratory glass slide coated with a thin layer of silicon oxide atop a reflective aluminum layer is used, and it is coated with a continuous layer of a hydrogel prepolymer solution that has anchoring moieties dispersed throughout. Solution A is prepared by mixing 0.075 g of Hypol PreMa G-50 (Dow Chemical Company) and a solution of 0.225 g of acetonitrile and 0.225 g of N-methyl-2-pyrrolidone. Solution B is prepared as 0.5 µM derivatized NTA chelator in 50 mM aqueous borate buffer at pH 8.2. This chelator has a primary amine that covalently binds in the crosslinked hydrogel. About 200 µL of Solution A is then mixed with 50 µL of Solution B causing polymerization to begin, and the resulting composition is coated onto the amine-treated glass slides. The hydrogel coating containing the chelator is carefully polymerized in a humidity box, at about 95% RH and room temperature, to avoid dehydration. This formulation polymerizes within about 2 hours at room temperature. After curing, the hydrogel slab is about 50 microns thick, and it is physically stable and strongly attached to the glass slide. The cured slide is then treated with an aqueous solution containing copper nitrate at a concentration at about 50 µM for 2 hours at room temperature to allow copper cations to be sequestered by the chelator molecules that are dispersed uniformly throughout the porous hydrogel slab. Following activation of the chelators in this manner, the slide is washed with 50 µM acetic acid solution containing 0.1 M KNO$_3$ (pH 4) for 1 hour and then rinsed with deionized H$_2$O. It is then dried to prepare it for microspotting to create a test microarray.

Microspotting is carried out to create a regular pattern of microspots on the surface of the activated hydrogel slab using 5 microliter glass microcapillary tubes. For test purposes, the tubes each contain green fluorescence protein to simulate probes, which are tagged with histidine-rich peptides that complex with the copper. The microspotted surface is allowed to incubate at room temperature for about 2 hours to effect attachment of these probes in this regular pattern of microspots across the surface of the cured hydrogel slab.

The microarrays are washed to remove any excess probe and then scanned with a charge coupled camera. Imaging shows uniformly lighted microspots in a regular pattern across the array surface, with no significant fluorescence emanating from the regions between the microspots; this indicates that non-specific binding to the hydrogel slab is not a problem and that the substrates are well-suited for the fabrication of highly sensitive microarrays.

EXAMPLE 2

The procedure set forth in Example 1 is repeated using a similar isocyanate-capped polyurethane prepolymer. However, this time solution B is prepared by as a 0.5 mM solution of streptavidin in 50 mM aqueous borate buffer at pH 8.2. Again, about 200 μL of Solution A is mixed with 50 μL of Solution B, and the resulting composition is coated as a continuous layer onto the amine-treated glass slides and allowed to polymerize as previously described.

Following curing, microspotting is carried out to create a microarray in the form of a regular pattern of microspots on the surface of the hydrogel slab, again using 5 microliter glass microcapillary tubes. For this test, the tubes each contain biotinlayted antibody for prostate-specific antigen (PSA) to be used as probes, as well known in this art. The microspotted surface is allowed to incubate at 25° C. for about 60 minutes to effect biotin-avidin attachment of these probes in a regular pattern across the surface of the cured hydrogel slab.

The microarrays are washed to remove any excess probe and then subjected to hybridization with an aqueous solution of PSA that is labeled with Cy-3 as a test target material; the labeled PSA selectively binds with the probes. Following incubation for about 60 minutes at 25° C., the array is washed and then imaged to obtain a fluorescent image of the surface of the microarray using a laser scanner (ScanArray® Lite, Perkin Elmer). Imaging shows uniformly lighted microspots in a regular pattern across the array surface, with no significant fluorescence emanating from the regions between the microspots; this indicates that non-specific binding to the hydrogel slab is not a problem and that the substrates are well-suited for the fabrication of highly sensitive microarrays.

It can be thus be seen that the employment of substrates having such a continuous slab of hydrogel can substantially increase the efficiency with which a microarray can be fabricated using the anchoring moieties uniformly dispersed throughout.

Although the invention has been described with regard to certain preferred embodiments, it should be understand that various changes and modifications as would be obvious to one having ordinary skill in this art can be made without departing from the scope of this invention which is set forth in the claims appended hereto. The disclosures of all U.S. patents and published patent applications set forth hereinbefore are expressly incorporated herein by reference.

Particular features of the invention are emphasized in claims which follow.

The invention claimed is:

1. A microarray for assaying for target material in a biological sample, which microarray comprises:

a solid, flat substrate having an upper surface that is functionalized with organic molecules, a polymerized hydrogel continuous layer of uniform thickness of at least about 5 microns completely covering an array region of the surface, the layer including anchoring moieties in the form of either organic chelators or streptavidin covalently linked to the hydrogel via isocyanate groups thereof and dispersed uniformly therethroughout, the hydrogel comprising a prepolymer of (a) PEG or PPG or a copolymer thereof of a molecular weight between about 5,000 and about 30,000 daltons and (b) difunctional and/or polyfunctional isocyanates, which prepolymer has active isocyanate groups present in an amount between about 0.1 meq/g and about 1 meq/g and is crosslinked by urea bonds into a porous hydrogel, and a plurality of different probes attached at distinct spatial locations throughout the at least about 5 micron thick hydrogel layer covering the upper surface to create a plurality of microspots, the probes being linked to the anchoring moieties in said polymerized hydrogel layer, and regions surrounding each of the microspots being essentially free from probes and resistant to non-specific binding of target materials.

* * * * *